United States Patent
Kipke et al.

(10) Patent No.: US 6,592,566 B2
(45) Date of Patent: Jul. 15, 2003

(54) METHOD FOR FORMING AN ENDOVASCULAR OCCLUSION

(75) Inventors: Daryl R. Kipke, Tempe, AZ (US); Timothy A. Becker, Chandler, AZ (US); Vance E. Collins, Tempe, AZ (US)

(73) Assignee: Arizona Board of Regents, Phoenix, AZ (US)

( * ) Notice: Subject to any disclaimer, the term of this patent is extended or adjusted under 35 U.S.C. 154(b) by 61 days.

(21) Appl. No.: 09/777,263

(22) Filed: Feb. 5, 2001

(65) Prior Publication Data

US 2001/0031978 A1 Oct. 18, 2001

Related U.S. Application Data

(60) Provisional application No. 60/180,109, filed on Feb. 3, 2000.

(51) Int. Cl.$^7$ .............................................. A61M 31/00
(52) U.S. Cl. ........................................ 604/508; 606/213
(58) Field of Search ................................ 604/508, 507, 604/93.01, 94.01, 264, 82; 424/423, 445, 78.08; 514/772.2; 602/43, 52; 128/DIG. 22; 606/213–221

(56) References Cited

U.S. PATENT DOCUMENTS

| | | | | |
|---|---|---|---|---|
| 5,614,204 A | * | 3/1997 | Cochrum | 128/DIG. 22 |
| 5,650,116 A | | 7/1997 | Thompson | |
| 5,762,959 A | * | 6/1998 | Soon-Shiong et al. | 424/422 |
| 6,033,401 A | * | 3/2000 | Edwards et al. | 606/214 |
| 6,306,169 B1 | * | 10/2001 | Lee et al. | 623/11.11 |

OTHER PUBLICATIONS

"Key Characterization Parameters of Alginate for Use in Biomedical and Pharmaceutical Application", Dornish et al., Pronova Biomedical, Oslo, Norway, pp. 1–9, undated.

Transvenous Embolization as the Primary Therapy for Arteriovenous Fistulas of the Lateral and Sigmoid Sinuses, Dawson et al., American Society of Neuroradiology, Mar. 1998, pp. 571–576.

"Transvenous Retrograde Nidus Sclerotherapy Under Controlled Hypotension", Massoud et al., Neurosurgery, vol. 45, No. 2, Aug. 1999, pp. 351–365.

"Effect of the Alginate Composition on the Biocompatibility of Alginate–Polylysine Microcapsules", De Vos et al., Biomaterials 1997, vol. 18, No. 3, pp. 273–278.

"Nonadhesive Liquid Embolic Agent for Cerebral Arteriovenous Malformations", Murayama et al., Neurosurgery, vol. 43, No. 5, Nov. 1998, pp. 1164–1175.

"Improved Biocompatibitity but Limited Graft Survival After Purification of Alginate for Microencapsulation of Pancreatic Islets", De Vos et al., Diabetologia, Springer–Verlag 1997, pp. 262–270.

"Biocompatibility of Mannuronic Acid–Rich Alginates", Klock et al., Biomaterials 1997, vol. 18, No. 10, 1997, pp. 707–713.

"Production of Purified Alginates Suitable for Use in Immunoisolated Transplantation", Klock et al., Applied Microbiology and Biotechnology, Springer–Verlag 1994, pp. 638–643.

* cited by examiner

Primary Examiner—Brian L. Casler
Assistant Examiner—Catherine Serke
(74) Attorney, Agent, or Firm—Snell & Wilmer, L.L.P.

(57) ABSTRACT

A method for forming an endovascular occlusion by controlling the injection parameters of a purified alginate liquid and a calcium chloride solution to meet and polymerize at a target site within the vascular system. Different types of injection techniques may be used with a preferred injection technique of simultaneous bi-directional injection where the purified alginate liquid is injected through a vein and the calcium chloride solution is injected through an artery.

31 Claims, 6 Drawing Sheets

| IMPLANT TIME (DAYS) | CHM | STD. DEV. | POLYMER TYPE CHG | STD. DEV. | PHM | STD. DEV. | PHG | STD. DEV. |
|---|---|---|---|---|---|---|---|---|
| 1 | 3.0 | 1.41 | 1.5 | 0.71 | 1.0 | 0.00 | 1.0 | 0.00 |
| 7 | 3.5 | 0.71 | 2.0 | 0.00 | 2.0 | 0.00 | 1.0 | 0.00 |
| 21 | 4.0 | 0.00 | 3.5 | 0.71 | 2.0 | 0.00 | 2.0 | 0.00 |
| 63 | 3.0 | 0.00 | 3.0 | 1.41 | 1.5 | 0.71 | 1.5 | 0.71 |
FIG.9
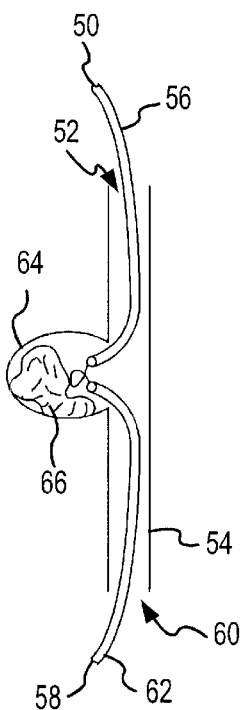
FIG.10
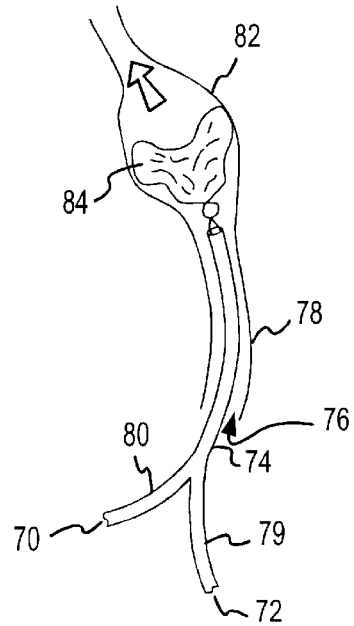
FIG.11

METHOD FOR FORMING AN ENDOVASCULAR OCCLUSION

CROSS-REFERENCE TO RELATED APPLICATIONS

This application claims the benefit of U.S. Provisional Application No. 60/180,109, filed Feb. 3, 2000.

FIELD OF THE INVENTION

The present invention relates generally to a method for forming an endovascular occlusion to treat conditions such as arteriovenous malformations, aneurysms, excessive blood supplied to tumors, control of massive vascular hemorrhaging, and other conditions which require an embolization to alleviate the condition. More particularly, the present invention relates to a method for forming an endovascular occlusion using calcium alginate by controlling the injections of a purified alginate liquid and a calcium chloride solution to meet and polymerize at a site within the vascular system targeted for occlusion.

BACKGROUND OF THE INVENTION

Endovascular polymer treatment is a new and growing field for achieving vascular occlusion of blood flow. With this technique, polymer materials are injected directly into blood vessels so that the polymer material will travel to the targeted site in the vascular system and polymerize to form an endovascular occlusion at the target site. Current endovascular embolizations use materials such as isobutyl-2-cyanoacrylate (IBCA), poly vinyl alcohol (PVA), ethanol, polylene threads, hyaluronic acid gels, and cellulose acetate to treat vascular defects such as arteriovenous malformations (AVMs) and aneurysms.

Many polymer materials used for endovascular embolization are toxic and typically require organic solvents that can damage and weaken blood vessel walls. Some endovascular polymer "glues" adhere to the vessel by damaging and infiltrating the wall of the blood vessel, thereby increasing the likelihood of hemorrhage. In addition, current polymer glues are difficult to control which results in the polymer gluing the inside of the delivery catheter and sometimes gluing the catheter to the blood vessel wall.

Calcium alginate is a two component polymer that exhibits high mechanical strength in its stable solid form and low viscosity in its injectable liquid form. This polymer consists of a natural polysaccharide gel component, alginic acid, which is derived from brown algae and is instantly cross-linked when contacted with calcium chloride to form calcium alginate. Alginate has many uses in bioengineering and can be used in polymer films, cell encapsulation, wound dressings, and surgical sponges, to name just a few. For example, U.S. Pat. No. 5,650,116 discloses a method for making medical devices such as stents, catheters, cannulas, plugs and constrictors from alginic acid, among other ionically cross-linkable polymers, and the crosslinking cation calcium. The cross-linkable polymer is introduced through a die to form a tube while the cross-linking ion in solution is simultaneously pumped through the formed tube. The formed tube is extruded from the die into a crosslinking ion solution to cross-link the formed tube which is used to make a stent, catheter, or cannula.

Calcium alginate may also be used as a vascular occlusion agent that is injected into a blood vessel for travel to a targeted site in the vascular system. For example, U.S. Pat. No. 5,614,204 describes angiographic vascular occlusion agents and a method for hemostatic occlusion. A liquid biopolymer gel in situ in contact with divalent cations is one example of a vascular occlusion agent that is described. The mode of administration includes dissolving the biopolymer in a solution that does not cause it to gel and injecting the bipolymer in liquid form to the site where the occlusion is needed. A calcium solution is independently added before, during or after the injection of the biopolymer. However, this mode can still result in either early polymerization or failure to occlude the targeted area. Other modes of administration include injecting a biopolymer solution and allowing it to act with calcium ions in the blood, combining the biopolymer with platelet-rich plasma and injecting it into a vessel, and ejecting a bipolymer solution from a catheter and dropping it into a calcium chloride solution followed by injecting the resulting solution through a catheter to the bleeding area. The same risks may also exist with these modes of administration.

Certain forms of alginate are considered biocompatible because of their natural polysaccharide structure. Alginate gels have an extremely high water content thereby allowing diffusion of the reactive component, calcium chloride, and biological fluids into the polymer. The reactive component calcium chloride is also considered biocompatible at certain dosages. Accordingly, although calcium alginate has previously been identified as an endovascular occlusion agent, there is a need for a method of administration which enables control of the occlusion agent to meet and polymerize at the target site.

BRIEF SUMMARY OF THE INVENTION

The present invention is directed to a new and flexible treatment option for endovascular occlusion that optimizes alginate with various microcatheter delivery systems. Calcium alginate, which is a biocompatible and mechanically stable, embolizing two component polymer, is selectively delivered to blood vessels from microcatheters to perform effective endovascular polymer occlusion. In one embodiment of the invention, separate polymer components are introduced from separate blood vessels and from opposite directions and are controlled to meet and polymerize at a specified point within the vascular system.

In another embodiment of the invention, separate polymer components are simultaneously introduced into the same blood vessel by a dual-lumen microcatheter and are controlled to meet and polymerize at the target site within the vascular system.

In yet another embodiment of the invention, staged injections of the separate polymer components may be controlled to meet and polymerize at a specified point within the vascular system.

One aspect of the invention involves utilizing a two-component polymer comprising a purified alginate having a high guluronic acid content. The alginate is purified by the following steps: 1) the alginate is dissolved in a chelant in an ice bath and the resulting solution is filtered through syringe filters, 2) the solution is placed in an ice bath and its pH is lowered to 3 to form an alginate precipitate, 3) the solution is filtered and the liquid is discarded, 4) a mixture of chloroform and butanol is added to the alginate precipitate and stirred for a predetermined time period to remove proteins interacting with the alginate, 5) the solution is filtered and the liquid is discarded, 6) the alginate precipitate is re-dissolved in deionized water and its pH is increased to 7 over a predetermined time period, 7) another chloroform and butanol mixture is added to the solution and stirred for a predetermined amount of time to remove remaining proteins, 8) the solution is then centrifuged to separate the water and alginate solution from the chloroform and protein solution and precipitated protein contaminants, 9) the top layer of water and alginate solution is aspirated off and ethanol is added to it to precipitate the purified alginate, 10) the purified alginate is filtered and dried, and 11) the purified alginate is sterilized with ethylene oxide.

In another aspect of the invention, the purified alginate is used to make a purified alginate solution where the purified alginate has a concentration of less than 3%. The purified alginate may be mixed with water or a solution comprised of water and radiological contrast agent to form the purified alginate solution. The purified alginate solution has physical characteristics which include low viscosity, high polymer yield, and high mechanical stability.

The viscosity of the unreacted purified alginate solution is preferably within a range of about 25 cP to 275 cP. The reacted purified alginate solution comprises a polymer yield within a range of about 25% to 75% and a mechanical stability within a range of about 14 kPa to 30 kPa with respect to 40% compression.

Another aspect of the invention includes a calcium chloride solution, acting as a crosslinking ion, having a calcium chloride concentration in the range of about 5% to 12%. The calcium chloride solution may be formed by dissolving calcium chloride in water or a solution comprised of water and radiological contrast agent.

The calcium alginate is optimized for forming an endovascular occlusion by controlling the injection rate, injection pressure, and viscosity of the purified alginate solution and the calcium chloride solution. Predetermined injection rates, injection pressures and viscosities for the two solutions are determined by the length, diameter, and surface area of the microcatheters that are used for injection after evaluating characteristics of the blood flow through the blood vessels in the targeted area.

BRIEF DESCRIPTION OF THE DRAWING FIGURES

The present invention will hereinafter be described in conjunction with the appended drawing figures where:

FIG. 2b is a schematic of the vessel diameters used for the PTFE vascular grafts used in the bench model shown in FIG. 2a;

FIG. 3b is a graph showing mechanical stability results utilizing the AVM bench scale model shown in FIG. 3a;

FIG. 9 is a table showing visual severity averages and standard deviations of polymer reactivity;

FIG. 10 is a schematic showing the simultaneous bi-directional injection of an alginate liquid and a calcium chloride solution through separate catheters into opposite blood vessels; and FIG. 11 is a schematic showing the simultaneous injection of an alginate liquid and a calcium chloride solution through a double lumen catheter into a blood vessel.

DETAILED DESCRIPTION OF EXEMPLARY EMBODIMENTS

Alginate forms a stable gel when reacted with a divalent solution such as calcium chloride. The alginate polymer begins to react immediately when contacted with calcium chloride and can be flow directed to block the vascular system. Alginate is non-adhesive and forms a stable structure that fills the vessel lumen and can withstand in vivo blood pressures without dislodging or degrading. Unlike many current endovascular occlusion materials, alginate exhibits biocompatible and non-adhesive properties thereby avoiding damage to the vessel wall. Instead, alginate fills the vascular space and creates an effective blockage in complex vascular beds or branching vascular systems. A large volume of alginate can be delivered to the vessel system to allow more complete occlusion without gluing the catheter to the vessel wall.

The present invention is directed to separately introducing and controlling the injections of a purified alginate liquid and a calcium chloride solution into a blood vessel so that they meet and polymerize at a target site within the vascular system. The purified alginate liquid and calcium chloride solution may each be simultaneously injected into separate blood vessels from opposite directions (bi-directional), may each be simultaneously injected through a dual lumen catheter into the same blood vessel, or may each be injected in stages into the same blood vessel. The injection rate, injection pressure and injectate viscosity are all controlled to enable the injectates (purified alginate liquid and calcium chloride solution) to meet and polymerize at the target site.

Figure 1:
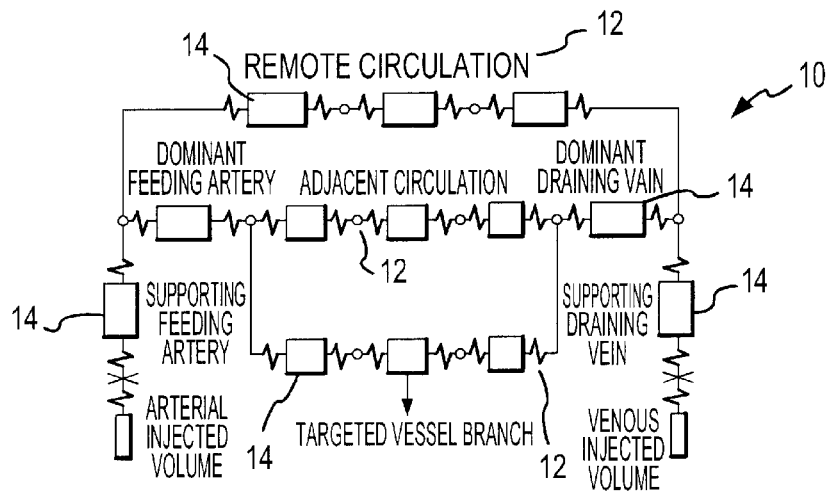
FIG. 1 is a diagram of an arteriovenous malformation (AVM) computer model.

In order to determine injection rates, injection pressures, and injectate viscosities, various AVM models were constructed. First, an AVM computer model was created as shown in FIG. 1 to determine the injection parameters and flow characteristics of a successful bi-directional injection technique. The simulation was a one-dimensional model 10 that calculated injection flow rates and volumes in three lumped vessel branches 12 consisting of thirteen predetermined cerebral compartments 14. The computer model predicted the response of the system to various injection parameters, including injection pressure, injection rate, and injectate viscosity and represented the initial step toward developing a polymer embolization technique consisting of polymer injection from the arterial (proximal) and venous (distal) sides of a vessel model.

The information collected from the AVM computer model enabled 1) the design of bench-scale models of a vascular system, based loosely on a cerebral AVM, to test the flow characteristics of the bi-directional injection technique and 2) the creation of a standardized procedure for testing the mechanical characteristics required of a polymer that is used as an endovascular occlusive agent.

Figure 2A:
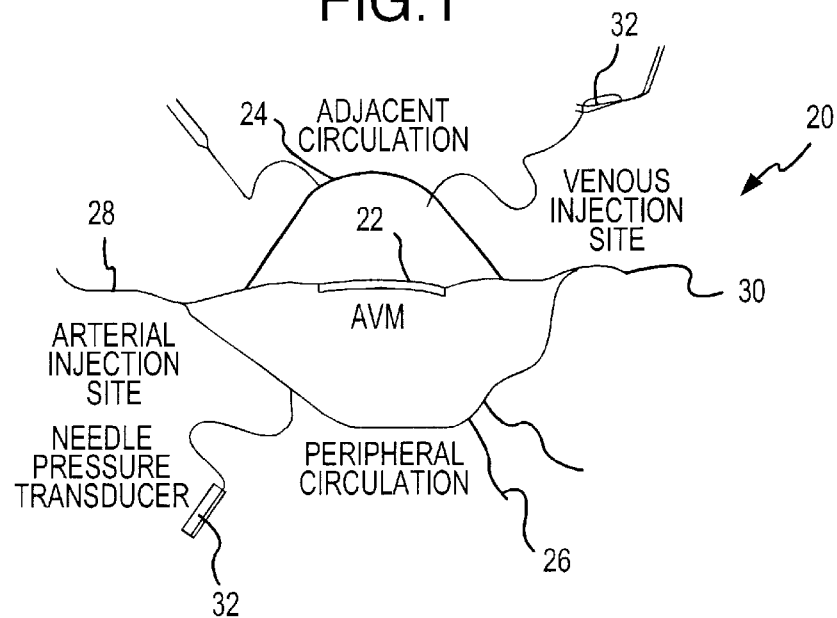
FIG. 2a is a fluoroscope image showing an AVM bench scale model utilizing PTFE vascular grafts.
Figure 2B:
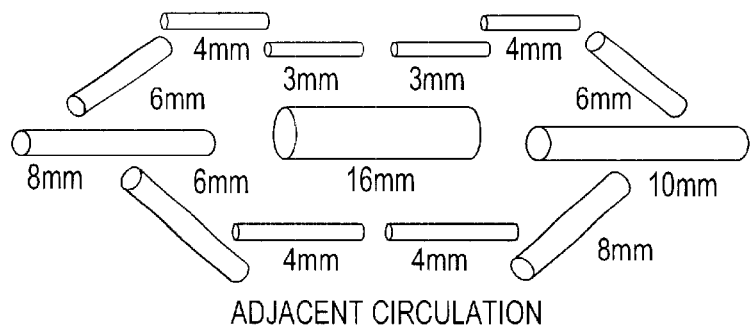

The flow patterns of bi-directional injections were analyzed using in vitro models. The fluoroscope images of the models shown in FIGS. 2a and 3a were constructed from polytetrafluoroethylene (PTFE) grafts supplied by Impra, Inc. located in Tempe, Ariz., with mechanical properties and compliance values similar to actual blood vessels. Experimental tests determined the flow resistance and compliance of each diameter of PTFE vascular graft and the grafts of varying diameter were assembled to construct a branching network as shown in FIG. 2b.

Pressure information collected from flow through the grafts was used in conjunction with fluoroscope images to determine fluid flow rates throughout the branches of the model. FIG. 2a depicts the entire model 20 including the AVM 22, the adjacent circulation 24, the peripheral circulation 26, the arterial injection site 28, the venous injection site 30, and pressure transducers 32. Computer simulations using the AVM computer model shown in FIG. 1 showed that the bi-directional injection of fluids would distribute throughout the computer model with 77% of the flow reaching the AVM, or targeted vessel shunt, and the rest flowing to the healthy peripheral and adjacent blood vessels. However, the AVM bench scale model shown in FIG. 2a showed that optimization of the flow rate and injectate volume could increase focal delivery of fluid to the AVM, or targeted vessel shunt, to above 95%; a 33% increase over the results from the AVM computer model.

A second major finding showed that over-injection of fluids caused a dramatic increase in flow to the peripheral system. Once the AVM, or vessel shunt, was filled, the fluid then propagated to the higher resistance peripheral pathways, thereby reducing focal delivery to the targeted vessel. The AVM bench scale model shown in FIG. 2a was used to successfully optimize the injection pressure, injection rate, and polymer viscosity required to obtain focal delivery of the embolizing polymer.

Figure 3A:
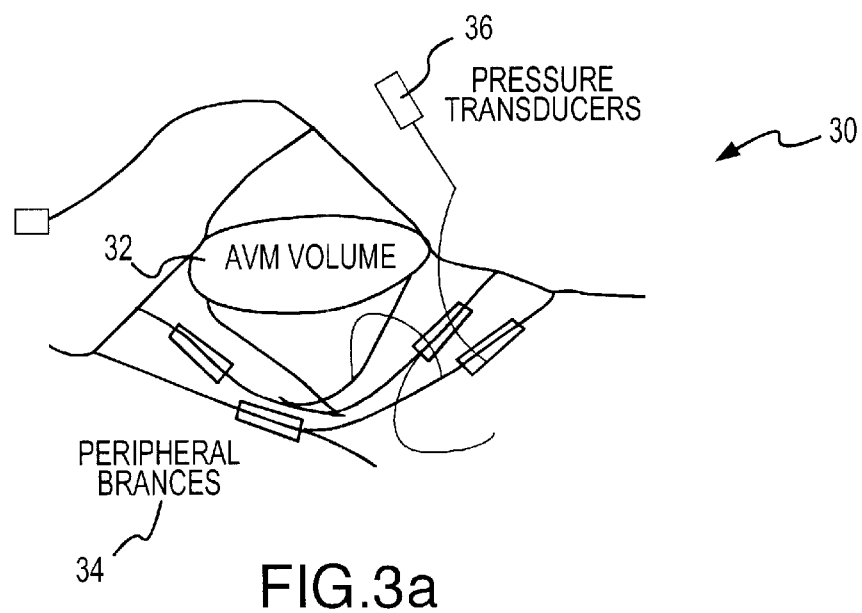
FIG. 3a is a fluoroscope image showing a second AVM bench scale model.
Figure 3B:
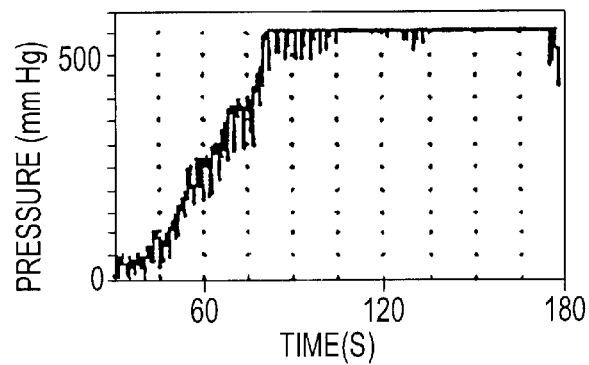

A second AVM bench scale model shown in FIG. 3a was constructed from a more complex grouping of grafts to test the mechanical stability of a polymer injected and polymerized within the vessel network. The second AVM bench scale model 30 shows AVM volume 32, peripheral branches 34 and pressure transducers 36. Crude, unoptimized calcium alginate was bi-directionally injected into the model 30 to test the effectiveness of the polymerization technique. Calcium alginate completely and consistently stopped flow through the vessel model. After vessel embolization, the model 30 was subjected to simulated in vivo pulsatile cerebral pressures with no signs of wear or fatigue. The polymer plug then withstood pulsatile pressures of 250 mm Hg (twice the normal cerebral pressure) for 48 hours. Results of the mechanical stability test using the second AVM bench model 30 are shown in FIG. 3b. FIG. 3b shows that the polymer also withstood pressures beyond 550 mm Hg, which was the saturation point of the pressure transducers.

Figure 4:
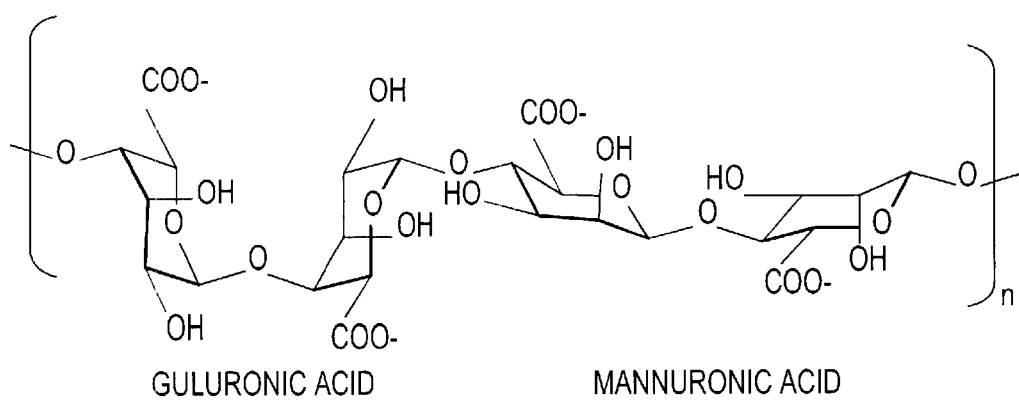
FIG. 4 is a schematic showing the chemical structure of alginate.

Calcium alginate was selected as the occlusion material in the present invention due to the high mechanical strength exhibited in its reacted solid form, low viscosity exhibited in its unreacted liquid form, and high biocompatibility. Alginate polymer is a natural polysaccharide gel derived from brown algae that can be instantly cross-linked when contacted with calcium chloride, thereby forming calcium alginate. Alginate is a copolymer consisting of blocks of mannuronic (M) and guluronic (G) acids in various arrangements along the polymer chain as can be seen in the chemical structure of alginate shown in FIG. 4. The concentration of G and M acids contribute to varied structural and biocompatibility characteristics. The concentration of G and M is noted by the G/M ratio; for example, alginate consisting of 60% G and 40% M acids has a G/M ratio of 60/40. The G/M ratio can vary from as high as 80/20 to as low as 30/70, depending solely on what species of algae the alginic acid is extracted from. The G/M ratio is independent of the purification process.

Figure 5A:
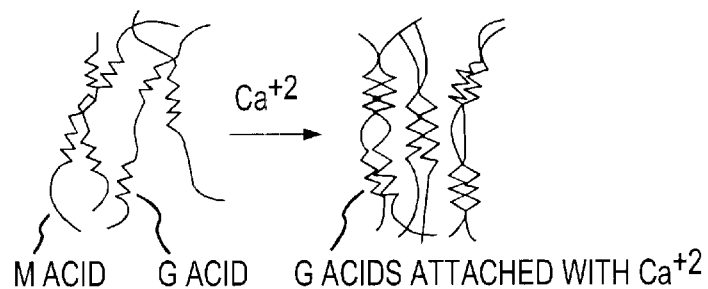
FIG. 5a is a schematic showing guluronic acid interaction with calcium ions.

The guluronic acid sites are active and can react with monovalent and divalent ions such as sodium and calcium, respectively. The mannuronic acid sections do not participate in the polymerization process. When reacted with sodium, the ion attaches to the guluronic acid block to form a stable, non-reactive form of alginate. This form of alginate is easily dissolved in water and can form solutions with low enough viscosities to allow endovascular injection. However, increasing the concentration of sodium alginate in water increases the interaction of the alginate chains, quickly increasing viscosity well above the injectable limit for modern microcatheters. Therefore, precise concentrations of alginate in solution are required for successful injection. When calcium ions are added in the form of calcium chloride, the increased free energy of calcium replaces the sodium with the calcium ions. Calcium is also divalent thereby providing two sites for guluronic acid attachment on each calcium ion. The result is a crosslinking of the alginate polymers interconnected by calcium ions to form a stable polymer gel as shown in FIG. 5a.

Figure 5B:
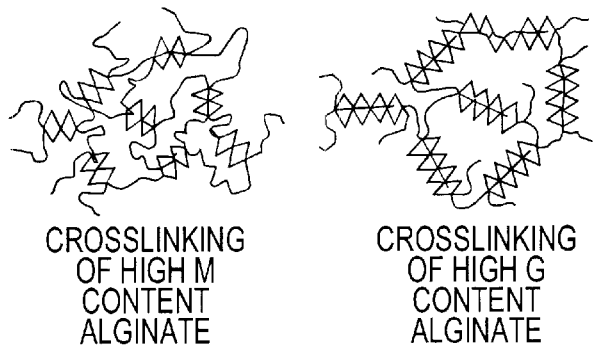
FIG. 5b is a schematic showing the matrix structure of mannuronic acid rich and guluronic acid rich alginates.

FIG. 5b shows the cross-linked matrix of high M content alginate and high G content alginate. Alginates with high M acid content form amorphous polymers with few attachment sites thereby resulting in a dense and complex gel structure with a low water content and a low polymer yield. High G acid content alginates have more sites for reaction thereby resulting in a structured cross-linked matrix. The matrix has space between the alginate chains that hold large volumes of water within the matrix thereby resulting in a high polymer yield. The only bi-product of the polymerization is the release of sodium ions and chloride ions which form saline.

Alginate was industrially purified (purified alginate was provided by Pronova Inc.) and purified in-house to determine whether pure alginates exhibit increased mechanical stability and/or increased biocompatibility. Alginate was purified in-house by carrying out the following steps:

1. Alginate was dissolved in a chelant (EGTA) in an ice bath to maximize the solubility of alginate, minimize alginate chain degradation, and minimize the solubility of contaminants. The solution was then filtered through syringe filters with a pore size of 5 micrometers to remove the majority of insoluble contaminants.
2. The alginate was again placed in an ice bath and the pH was lowered to 3 with 2M hydrochloric acid (HCl). The alginate is not soluble at low pH. Therefore, the alginate precipitates and many dissolved contaminants remain in solution. The remaining solution was filtered with a Buchner filter and the liquid was discarded.
3. A mix of chloroform (20 ml per 100 ml) and butanol (5 ml per 100 ml) was added to the alginate precipitate and stirred for 30 minutes to remove proteins interacting with the alginate. The solution was again filtered with a Buchner filter and the liquid was discarded.
4. The alginate precipitant was re-dissolved in deionized water and 0.5M sodium hydroxide (NaOH) was added over a one hour period until the alginate was at a pH of 7 and fully dissolved.

5. Chloroform (20 ml per 100 ml) and butanol (5 ml per 100 ml) were again added and stirred for 30 minutes to remove any remaining proteins.
6. The solution was then centrifuged at 3500 rpm for 10 minutes to separate the water-alginate solution from the higher density chloroform-protein solution and precipitated protein contaminants.
7. The top layer of the centrifugate was purified alginate which was aspirated off and placed in 95% ethanol (2:1 ethanol:alginate volume) to precipitate the purified alginate.
8. The purified alginate precipitate was filtered off and dried overnight.
9. The alginate was sterilized with ethylene oxide to ready for implantation.

A similar purification was performed at the industrial level by Pronova Inc. on the high G acid content alginate. Pronova's purification included a final filtration of the liquid polymer through a 0.2 micrometer filter to obtain sterility before precipitating and drying the alginate. The in-house purification method did not include a final filtration but instead was precipitated and dried, and then sterilized with ethylene oxide gas.

A functional polymer plug used to occlude a blood vessel must withstand the compressive forces of blood pressure. Four types of alginate were tested for compressive resistance: purified alginate with a high M acid content (Pure-High M), purified alginate with a high G acid content (Pure-High G), crude alginate with a high M acid content (Crude-High M), and crude alginate with a high G acid content (Crude-High G).

An Instron testing machine was used for running compression tests. A polymer sample was situated between two metal plates and compressed at a set compression rate until flat (0.5 in/min to a maximum force of 500 lbs.). Force versus displacement data was gathered by the Instron computer during compression at 10 samples/second.

The Instron compression head contains a force plate that measures the polymer's resistance to compression in lbf. Polymer compressive resistance is determined by graphing polymer resistive pressure (mm Hg) versus % compression of the polymer sample. Pressure is calculated by dividing the surface area of the polymer sample by the resistive force measured by the Instron machine. Percent compression is calculated by the following equation:

$$\% \text{ compression} = 100(t_i - t_f)/t_i$$

where $t_i$ is the initial polymer thickness and $t_f$ is the polymer thickness after compression.

Each polymer sample tested for compressive strength must have a consistent shape in order to accurately calculate pressure and % compression. The ideal shape is a cylinder with a known surface area and a known initial thickness. The change in polymer diameter with % compression was modeled to determine the instantaneous surface area so that compressive pressure could be modeled throughout the compression test. A constant area compression was also run and used as a comparison. A cylindrical plate with a constant surface area, smaller than the area of the alginate sample, was used to compress the remaining alginate samples.

Figure 6A:
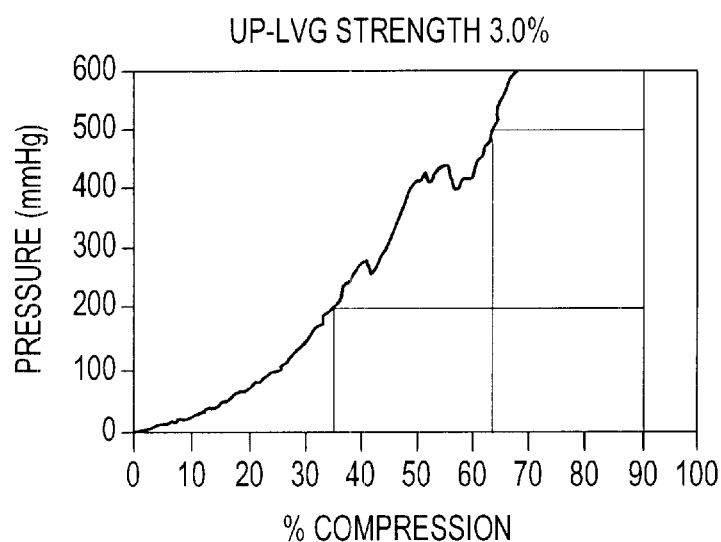
FIG. 6a is a graph showing high strength ratio alginate.
Figure 6B:
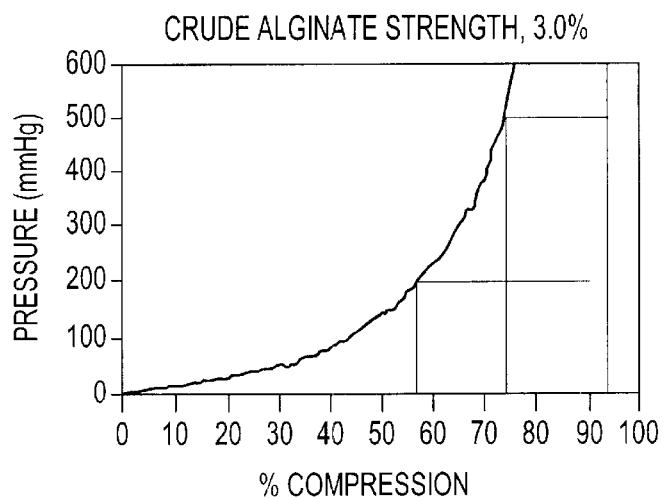
FIG. 6b is a graph showing low strength ratio alginate.

With the polymer diameter versus the polymer compression known, the force versus displacement data could be converted to pressure versus % compression as shown in FIGS. 6a and 6b. From the pressure versus % compression graph, the resistance of the polymer samples to a 200 mm Hg pressure and 500 mm Hg pressure was determined. 200 mm Hg is twice the pressure found in the cerebrovascular system, and 500 mm Hg was selected as a maximum pressure near the failure point of the polymer samples. The strength at 200 mm Hg and at 500 mm Hg was represented as a strength ratio. The ratio was calculated as the difference between the maximum % compression minus the % compression at 200 mm Hg and 500 mm Hg, respectively, all divided by the maximum % compression reached after 500 lbs. of force. The ratios could then be used to compare the strengths of various alginates and alginate concentrations. A high strength ratio alginate is shown in FIG. 6a and a low strength ratio alginate is shown in FIG. 6b.

Figure 7A:
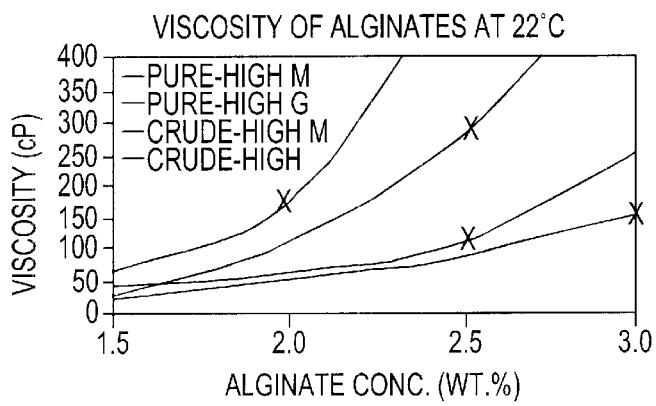
FIG. 7a is a graph showing the viscosity of tested alginates.
Figure 7B:
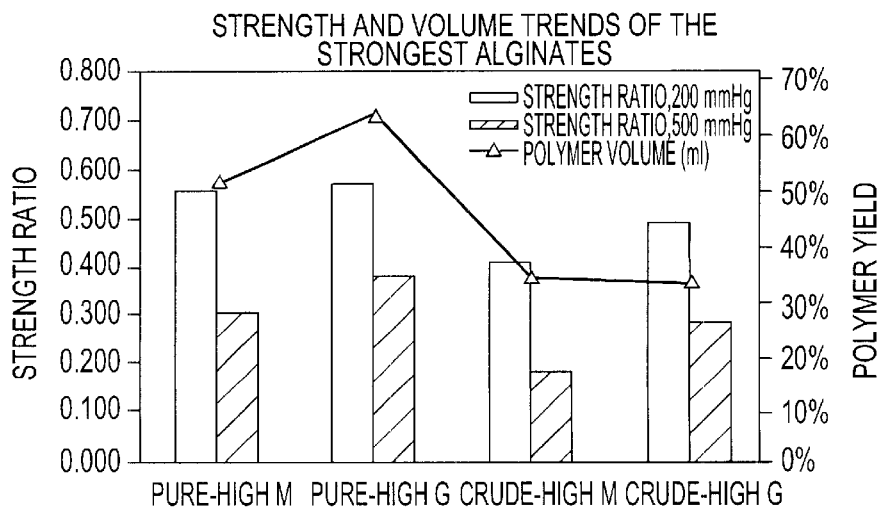
FIG. 7b is a graph showing maximal strength and polymer yields of alginates.

Larger ratios correspond to high strength polymers. Polymers with the greatest compressive resistance will reach higher pressures at lower levels of compression. However, weak, unstructured polymers cannot resist compressive forces and will deform (large % compression) before building up resistive pressure to the applied compressive force. The following information was derived from the compressive data and the initial and final polymer sample dimensions: the strength ratio at 200 mm Hg, the strength ratio at 500 mm Hg, the polymer gel volume, and the polymer's final compressed volume. The most desirable and highest strength polymers have the highest strength ratios, the largest initial gel volume (high polymer yield), the largest final compressed volume, and have a liquid viscosity of 120 cP or less. The viscosity of the tested alginates and the maximal strength and polymer yields of the alginates are shown in FIGS. 7a and 7b, respectively. As seen in FIGS. 7a and 7b, pure alginate with a high G acid content has the highest strength, the maximum polymer yield in its solid form, and the lowest polymer viscosity in its liquid form.

Alginates with high mannuronic acid content were previously thought to have high polymer strength but low biocompatibility while alginates with high guluronic acid content were believed to form lower strength polymers while exhibiting higher biocompatibility. However, others have cited the opposite result and there is no consensus as to which form of polymer is best for in vivo use. Newer findings are crediting alginate purification rather than alginate structure as the key to polymer biocompatibility and strength. Purification removes contaminants and proteins (i.e. phenols and endotoxins) that can cause an undesirable immunoresponse. Purification also removes components that can interfere with and inhibit the polymerization process. Other impurities are thought to contribute to bioreactivity but many of these impurities have not yet been identified. Therefore, various forms of purification of alginate can have an impact on the effective removal of impurities. Differences in purification may explain some of the conflicting results found in many published alginate biocompatibility studies.

The chemical structure of calcium alginate varies depending on where it was extracted. Alginate purity and structure can have significant effects on the resulting polymer biocompatibility. A biocompatible polymer exhibits little or no tissue reaction, minimal immune response, limited thrombus formation, and reduced hemolysis of blood cells. Any kidney and tissue reaction near the polymer is rated on a scale of severity. Polymer encapsulation, organ and tissue adhesion, and tissue necrosis are strong indicators of polymer incompatibility.

Toxicity and histological tests were performed on calcium alginate to determine tissue reactivity and endovascular biocompatibility with respect to alginate structure and purity. The short- and long-term tissue reactivity of calcium alginate was tested by injecting the polymer into the fat capsule surrounding the kidney of rat models. Polymer reactivity was tested 1 day, 1 week, 3 weeks, and 9 weeks post implant with visual tissue reactivity inspection and histological staining. At the end of each polymer implant study, the polymer and kidney are harvested along with the control kidney. Visual biocompatibility consists of ranking the reactivity of the kidney and surrounding tissue on a scale of 0 to 4; 0 to 1 being little or no reaction, adhesion, or encapsulation and 4 being major adhesion, encapsulation, and/or tissue necrosis.

Figure 8A:
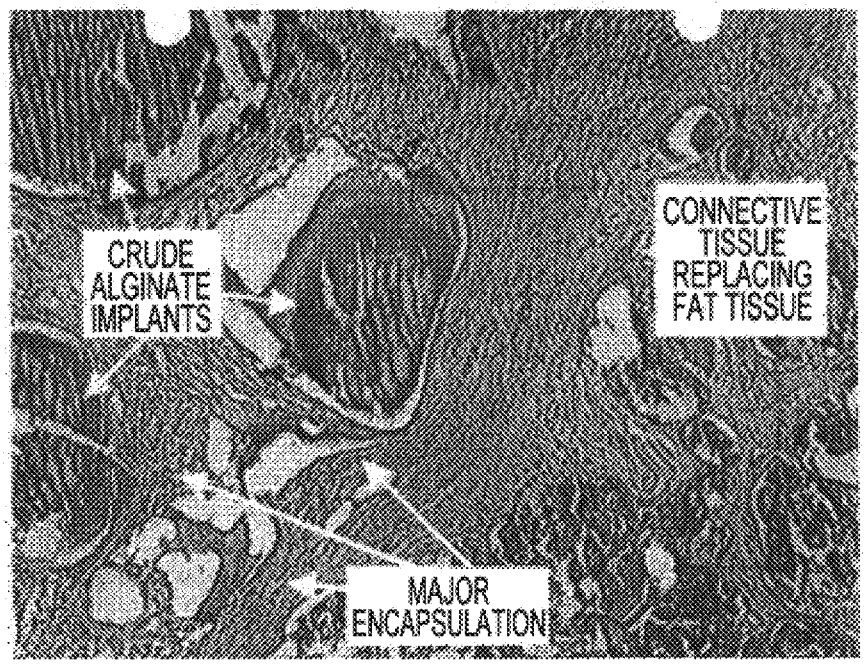
FIG. 8a is a micrograph picture showing a kidney after injection of crude calcium alginate into the fat capsule surrounding the kidney.
Figure 8B:
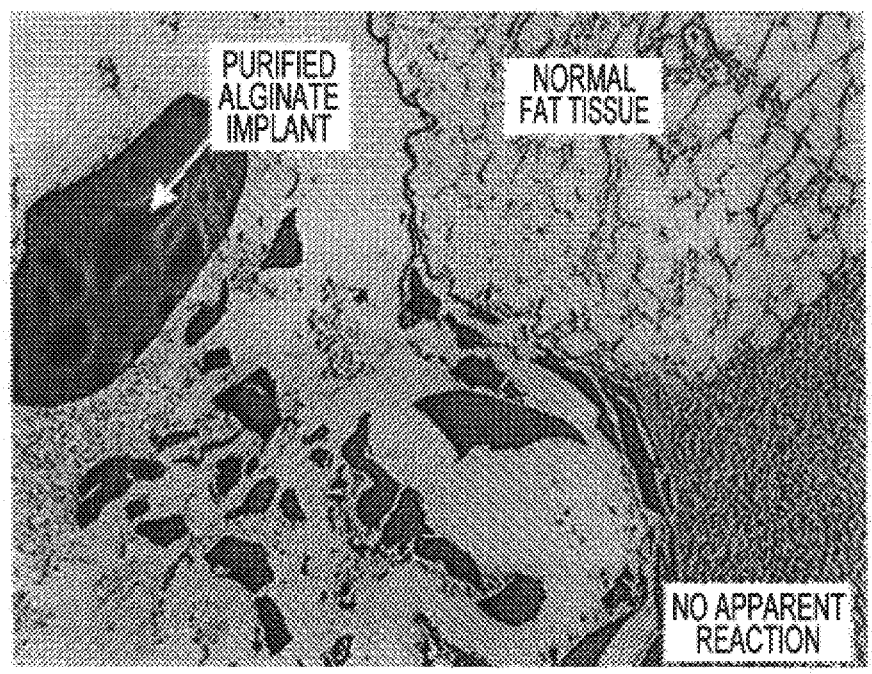
FIG. 8b is a micrograph picture showing a kidney after injection of pure calcium alginate into the fat capsule surrounding the kidney.

FIGS. 8a and 8b show a visual comparison of the change in kidney sizes and extent of tissue reactivity apparent from a crude alginate injection and a PHG (obtained from Pronova Biomedical, Oslo, Norway, UP-LVG) alginate injection. The crude polymer kidney is swollen and the surrounding tissue is highly encapsulated and discolored while the UP-LVG kidney is normal in size and color and the surrounding tissue is minimally encapsulated with no discoloration. Initial histology slides also verify that purified alginate induces a minimal immune response where crude alginate can cause major encapsulation and mobilization of lymphocytes.

FIG. 9 is a table showing the cellular reactivity of purified and crude alginates with varied levels of G and M acid contents. As seen in FIG. 9, crude alginate has high reactivity and alginates with high M acid content induce a faster immune response than high G acid polymers. However, the overall reactivity of crude alginate is consistently high (severity of 3 to 4) over the entire study. Purified alginates exhibit a significantly lower immune response. The overall reactivity remains consistent among the two alginic acid concentrations (severity of 1 to 2), and the high M content alginate again exhibits a faster immune response. From the data in FIGS. 7a, 7b, and 9, it can be concluded that purified alginates with high G content have minimal biological reaction as well as low viscosity, high polymer yield, and high mechanical stability when used for endovascular embolization.

The four types of tested alginates are shown bracketed in Table I to help determine the optimal material characteristics for endovascular injection.

TABLE I

Experimental determination of the optimal biocompatibility and mechanical stability of various forms of alginate

| | Material Optimization | | | | | |
|---|---|---|---|---|---|---|
| acceptable limits: | Biocom. short-term <3 | Biocom. long-term <3 | Viscosity @ 22' C. <120 | Strength @ 200 >0.45 | Strength @ 500 >0.225 | % Yield >50% |

| % conc. | Biocom. short | Biocom. long | Visc. (cP) | std. dev. +/− | Strength @ 200 | std. dev. +/− | Strength @ 500 | std. dev. +/− | Yield | std. dev. +/− | Overall |
|---|---|---|---|---|---|---|---|---|---|---|---|
| | | | | | Pure-High G | | | | | | |
| 3.5 | | | | | | | | | | | |
| 3.0 | *1* | *2* | *253* | *2.8* | *0.583* | *0.032* | *0.406* | *0.076* | *77.4* | *3.2* | *failed* |
| 2.5 | 1 | 2 | 113 | 2.1 | 0.550 | 0.058 | 0.390 | 0.037 | 68.1 | 6.9 | passed |
| 2.0 | 1 | 2 | 71 | 3.1 | 0.488 | 0.025 | 0.285 | 0.047 | 60.5 | 8.8 | passed |
| 1.5 | *1* | *2* | *45* | *5.0* | *0.473* | *0.110* | *0.165* | *0.021* | *54.6* | *12.3* | *failed* |
| 1.0 | | | | | | | | | | | |
| | | | | | Crude-High G | | | | | | |
| 3.5 | | | | | | | | | | | |
| 3.0 | | | | | | | | | | | |
| 2.5 | *2* | *4* | *800* | *50* | *0.689* | *0.041* | *0.535* | *0.031* | *54.4* | *3.5* | *failed* |
| 2.0 | *2* | *4* | *540* | *15* | *0.385* | *0.065* | *0.224* | *0.065* | *57.9* | *2.8* | *failed* |
| 1.5 | *2* | *4* | *178* | *3.4* | *0.503* | *0.028* | *0.301* | *0.018* | *33.8* | *4* | *failed* |
| 1.0 | *2* | *4* | *69* | *4* | *0.565* | *0.043* | *0.337* | *0.061* | *28.8* | *3.4* | *failed* |
| | | | | | Pure-High M | | | | | | |
| 3.5 | *1* | *2* | *275* | *7.1* | *0.587* | *0.016* | *0.355* | *0.041* | *49* | *1.5* | *failed* |
| 3.0 | *1* | *2* | *158* | *2.5* | *0.534* | *0.097* | *0.328* | *0.090* | *53.5* | *6.7* | *failed* |
| 2.5 | *1* | *2* | *95* | *3* | *0.481* | *0.069* | *0.215* | *0.030* | *42.3* | *4* | *failed* |
| 2.0 | *1* | *2* | *56* | *2.1* | *0.411* | *0.088* | *0.202* | *0.035* | *34.1* | *3.7* | *failed* |
| 1.5 | | | | | | | | | | | |
| 1.0 | | | | | | | | | | | |
| | | | | | Crude-High M | | | | | | |
| 3.5 | | | | | | | | | | | |
| 3.0 | *3* | *4* | *563* | *9.5* | *0.486* | *0.105* | *0.306* | *0.120* | *45.8* | *5.4* | *failed* |
| 2.5 | *3* | *4* | *283* | *7* | *0.446* | *0.072* | *0.243* | *0.064* | *36.8* | *5.7* | *failed* |
| 2.0 | | | | | | | | | | | |
| 1.5 | | | | | | | | | | | |
| 1.0 | | | | | | | | | | | |

*italics*: overall sample concentration deemed inadequate
underlined: specific sample factor that was inadequate
bold: overall sample concentration deemed acceptable An in vivo rabbit kidney model was used for alginate occlusion. Pure-High G alginate was injected into the renal vessels of a rabbit model to determine the extent of endovascular occlusion. Four types of alginate injection techniques were utilized. First, a bi-directional injection technique was used as shown in FIG. 10. FIG. 10 shows an alginate liquid 50 introduced into one end 52 of a blood vessel 54 via a first catheter 56 and a calcium chloride solution 58 introduced into an opposite end 60 of the blood vessel 54 via a second catheter 62. The alginate liquid 50 and calcium chloride solution 58 meet and polymerize at the site of the blood vessel defect 64 to form a calcium alginate gel 66. In the rabbit model, the renal vessels were catheterized and the polymer was injected through the renal vein while the calcium chloride reactive component was injected through the renal artery.

Second, the alginate liquid and calcium chloride solution were injected via a dual lumen catheter through the same end of a blood vessel as shown in FIG. 11. FIG. 11 shows an alginate liquid 70 and a calcium chloride solution 72 introduced into a dual lumen catheter 74 and injected into the same end 76 of a blood vessel 78. The alginate liquid 70 and calcium chloride solution 72 meet within the catheter 74 after leaving their separate lumens 79, 80 and polymerize at the site of the blood vessel defect 82 to form a calcium alginate gel 84 which stops the blood flow.

In the third injection technique, the polymer was delivered by a staged arterial injection with the alginate liquid injected first, followed by the injection of calcium chloride solution through the same catheter lumen. The fourth injection technique delivers the polymer by a staged venous injection with the alginate liquid injected first, followed by the injection of the calcium chloride solution through the same lumen catheter.

In each case a purified alginate having a high G acid content was used to form the alginate liquid and the alginate was successfully delivered into the vascular bed of the kidney and polymerized, forming a stable vascular plug that stopped all flow into and out of the kidney model. Alginate injectability depends on the inherent polymer characteristics of viscosity and flow rate. Microcatheter diameter, length, and surface tension (catheter resistance) dictate what viscosities and flow rates can be injected at specific injection pressures. Hagen-Poiseuille flow equations $Q=\Delta P/R$ and $R=128\,\mu L/(\pi d^4)$, where Q is the flow, $\Delta P$ is the microcatheter pressure, R is the flow resistance, $\mu$ is the alginate viscosity, L is the catheter length, and d is the microcatheter diameter. These equations can be used as long as catheter surface tension is included as a coefficient in the resistance (R) which is significant when using small diameter microcatheter lumens. The flow characteristics of various microcatheter diameters comprised of Teflon tubing as well as different microcatheter materials obtained from different vendors are included in Table II.

TABLE II

Flow properties for polymer injection through various catheter diameters and overall resistances.

|  | Catheter I.D. (in) | Catheter L (cm) | Resistance/L (psi*min/cm^4) | Error % | Viscosity (cP) | Pressure (psi) | Flow Rate (ml/min) |
|---|---|---|---|---|---|---|---|
| Teflon | 0.034 | 150 | 0.0031 | 10.6 | 1 | 0.63 | 5 |
|  |  |  |  |  | 91 | 47.1 | 100 |
|  | 0.022 | 150 | 0.0099 | 8.5 | 1 | 1.04 | 2 |
|  |  |  |  |  | 91 | 89.1 | 60 |
|  | 0.018 | 150 | 0.0210 | 8.5 | 1 | 1.13 | 1 |
|  |  |  |  |  | 91 | 126.2 | 40 |
|  | 0.012 | 150 | 0.0835 | 11.3 | 1 | 5.75 | 1 |
|  |  |  |  |  | 91 | 250.4 | 20 |
| Renegade | 0.021 | 150 | 0.0115 | 2.3 | 1 | 4.04 | 2.5 |
|  |  |  |  |  | 91 | 103.7 | 60 |
| Spinnaker | 0.0175 | 165 | 0.0179 | 4.3 | 1 | 4.2 | 1.5 |
|  |  |  |  |  | 91 | 118.3 | 40 |
| Excel | 0.017 | 150 | 0.0256 | 4.9 | 1 | 2.56 | 0.75 |
|  |  |  |  |  | 91 | 153.3 | 40 |

The present invention is directed to a method for forming an endovascular occlusion comprising the steps of controlling the injection parameters of a purified alginate liquid and a calcium chloride solution to meet and polymerize at a target location within the vascular system. As seem in Table I, the purified alginate liquid comprises a purified alginate concentration less than 4% and preferably within the range of about 2.0% to 2.5%. Purified alginate with a concentration of less than 2% possesses decreased mechanical stability in its reacted form thereby allowing for greater perfusion into the vessel defect. The calcium chloride solution comprises a calcium chloride concentration preferably within a range of 5% to 15%. The purified alginate liquid preferably comprises a viscosity within a range of about 25 cP to 275 cP but is subject to change depending upon the physical characteristics of the microcatheter through which it is injected. The reacted purified alginate liquid comprises a polymer yield within the range of about 25% to 75% and mechanical stability within a range of about 14 kPa to 30 kPa with respect to 40% compression but both are subject to change depending upon the physical characteristics of the microcatheter through which it is injected.

The two-component purified calcium alginate polymer provides greater flexibility and control of the polymerization process. The calcium alginate does not adhere to the inside or the outside of the catheter because the reactive component and the polymer are separate until they leave the catheter, and the resulting polymer is non-adhesive and non-destructive. The two-component alginate polymer can be injected from the catheters under precise control of the injection parameters, namely injectate flow rate, injection pressure, and polymer viscosity. The methods of the present invention provide focal delivery of the two component polymer to the blood vessel while minimizing polymer flow to the peripheral vasculature. The components of the polymer will mix and polymerize within the blood vessel system to provide permanent occlusion.

The foregoing description is of preferred embodiments of the subject invention. It will be appreciated that the foregoing description is not intended to be limiting; rather, the preferred embodiments set forth herein merely set forth exemplary applications of the subject invention. It will be appreciated that various changes, deletions, and additions may be made to the components and steps discussed herein, without departing from the spirit and scope of the invention as set forth in the appended claims.

We claim:

1. A method for forming an endovascular occlusion comprising the step of controlling a simultaneous injection of a purified alginate liquid having a high guluronic acid content and a calcium chloride solution to a targeted area within a vascular system wherein at least one of an injection rate, an injection pressure, and a viscosity of said purified alginate liquid and said calcium chloride solution are controlled.

2. The method of claim 1 wherein said purified alginate liquid comprises purified alginate in a concentration of less than 3.5%.

3. The method of claim 2 wherein the concentration of purified alginate liquid with a maximum mechanical stability, a minimal viscosity, and a minimal volume of contrast agent is preferably in a range of about 2.0% to 2.5%.

4. The method of claim 1 wherein said calcium chloride solution comprises calcium chloride in a concentration of about 5% to 15%.

5. The method of claim 1 wherein said purified alginate liquid comprises physical characteristics which include low viscosity, high polymer yield, and high mechanical stability.

6. The method of claim 5 wherein said purified alginate liquid comprises a viscosity within a range of about 25 cP to 275 cP.

7. The method of claim 5 wherein said purified alginate liquid comprises a polymer yield within a range of about 25% to 75% after polymerizing with said calcium chloride solution.

8. The method of claim 5 wherein said purified alginate liquid comprises a mechanical stability within a range of about 14 kPa to 30 kPa with respect to 40% compression after polymerizing with said calcium chloride solution.

9. The method of claim 1 wherein said purified alginate liquid and said calcium chloride solution are injected into a blood vessel using a microcatheter at a predetermined injection rate, a predetermined injection pressure and a predetermined viscosity.

10. The method of claim 9 wherein said predetermined injection rate, injection pressure and viscosity are determined by a length, a diameter and a surface tension of the microcatheter.

11. The method of claim 1 wherein said simultaneous injection is performed by bi-directional injection wherein the purified alginate liquid is injected into a vein and the calcium chloride solution is injected into an artery.

12. The method of claim 1 wherein said simultaneous injection is performed by using a dual-lumen catheter wherein each lumen contains either the purified alginate liquid or the calcium chloride solution which are both injected into a vein.

13. A method for forming an endovascular occlusion comprising the step of controlling at least one of an injection rate, an injection pressure, and a viscosity of a purified alginate liquid and a calcium chloride solution to meet and polymerize at a target location within a vascular system.

14. The method of claim 13 comprising the step of performing a simultaneous bi-directional injection wherein the purified alginate liquid is injected through a vein and the calcium chloride solution is injected through an artery.

15. The method of claim 14 wherein the step of performing the bi-directional injection comprises injecting predetermined viscosities of the purified alginate liquid and the calcium chloride solution using two separate microcatheters, each at a predetermined injection rate and a predetermined injection pressure.

16. The method of claim 15 wherein said predetermined injection rates, injection pressures and viscosities are determined by a length, a diameter and a surface tension of the microcatheters.

17. The method of claim 13 comprising the step of simultaneously injecting the purified alginate liquid and calcium chloride solution through a dual-lumen catheter.

18. The method of claim 17 wherein the injection step comprises injecting predetermined viscosities of the purified alginate liquid and the calcium chloride solution at predetermined injection rates and predetermined injection pressures.

19. The method of claim 18 wherein said predetermined injection rates, injection pressures and viscosities are determined by a length, a diameter and a surface tension of the microcatheters.

20. The method of claim 13 wherein said purified alginate liquid comprises purified alginate in a concentration of less than 4%.

21. The method of claim 20 wherein the concentration of purified alginate liquid is preferably in a range of about 2.0% to 2.5%.

22. The method of claim 13 wherein the calcium chloride solution comprises calcium chloride in a concentration of about 5% to 15%.

23. A method for forming an endovascular occlusion comprising the steps of:

purifying an alginate;

mixing water with the purified alginate to obtain a purified alginate liquid having a concentration of purified alginate that is less than 4%;

preparing a calcium chloride solution having calcium chloride in a concentration of about 5% to 15%;

determining a viscosity, injection rate, and injection pressure for the purified alginate liquid;

determining a viscosity, injection rate, and injection pressure for the calcium chloride solution; and injecting the purified alginate liquid and calcium chloride solution at their predetermined viscosities, injection rates, and injection pressures, respectively, to a target site within the vascular system.

24. The method of claim 23 wherein said injecting step comprises a simultaneous bi-directional injection of the purified alginate liquid and the calcium chloride solution through two separate microcatheters with the purified alginate liquid injected into a vein and the calcium chloride solution injected into an artery.

25. The method of claim 23 wherein said injecting step comprises a simultaneous injection of the purified alginate liquid and the calcium chloride solution through a dual-lumen microcatheter and into a vein.

26. The method of claim 23 wherein the injection step comprises staged injections of the purified alginate and the calcium chloride solution through a microcatheter and into an artery or a vein.

27. The method of claim 23 wherein the step of purifying an alginate comprises the steps of:
 a) dissolving the alginate in a chelant in an ice bath and filtering a solution resulting therefrom through syringe filters;
 b) placing the solution in an ice bath and lowering its pH to 3 to form an alginate precipitate;
 c) filtering the alginate precipitate from the solution;
 d) adding a mixture of chloroform and butanol to the alginate precipitate and stirring for a predetermined time period to remove proteins interacting with the alginate thereby forming a second solution containing the alginate precipitate;
 e) filtering the alginate precipitate from the second solution;
 f) re-dissolving the alginate precipitate in deionized water and increasing the pH to 7 over a predetermined time period;
 g) adding another chloroform and butanol mixture and stirring for a predetermined time period to remove remaining proteins thereby forming a third solution;
 h) centrifuging the third solution to separate the water and alginate solution from the chloroform and protein solution and precipitated protein contaminants;
 i) aspirating off the top layer of water and alginate solution and adding ethanol to precipitate the purified alginate;
 j) filtering and drying the purified alginate; and
 k) sterilizing the purified alginate with ethylene oxide.

28. A method for forming an endovascular occlusion comprising the step of staging an injection of a purified alginate liquid having a high guluronic acid content and a calcium chloride solution through a same blood vessel to a target site using a microcatheter at a predetermined injection rate, predetermined injection pressure, and predetermined viscosity for the purified alginate liquid.

29. The method of claim 28 wherein said predetermined injection rate, injection pressure, and viscosity are determined by a length, a diameter, and a surface tension of the microcatheter.

30. The method of claim 28 wherein said purified alginate liquid comprises purified alginate in a concentration of less than 4%.

31. The method of claim 30 wherein the concentration of purified alginate liquid is preferably in a range of about 2.0% to 2.5%.

* * * * *